US00PP26277P3

(12) United States Plant Patent
Lee

(10) Patent No.: US PP26,277 P3
(45) Date of Patent: Dec. 29, 2015

(54) ***RHODODENDRON* PLANT NAMED 'HOMLEC'**

(50) Latin Name: ***Rhododendron* hybrid**
Varietal Denomination: HOMLEC

(71) Applicant: Robert Edward Lee, Independence, LA (US)

(72) Inventor: Robert Edward Lee, Independence, LA (US)

( * ) Notice: Subject to any disclaimer, the term of this patent is extended or adjusted under 35 U.S.C. 154(b) by 175 days.

(21) Appl. No.: 13/998,423

(22) Filed: Oct. 30, 2013

(65) Prior Publication Data

US 2015/0121586 P1 Apr. 30, 2015

(51) Int. Cl.
*A01H 5/02* (2006.01)

(52) U.S. Cl.
USPC ..... Plt./240

(58) Field of Classification Search
USPC ..... Plt./240
See application file for complete search history.

*Primary Examiner* — Anne Grunberg
(74) *Attorney, Agent, or Firm* — Cassandra Bright

(57) ABSTRACT

A new and distinct *Rhododendron* cultivar named 'HOMLEC' is disclosed, characterized by distinctive Red-Orange flowers. Plants bloom Spring, Summer and Fall. The new cultivar is a *Rhododendron*, suitable for ornamental garden purposes.

1 Drawing Sheet

Latin name of the genus and species: *Rhododendron* hybrid.

Variety denomination: 'HOMLEC'.

BACKGROUND OF THE INVENTION

The new cultivar is a product of a planned breeding program by the inventor, Robert Edward Lee. The inventor's intention was to develop *Rhododendron* hybrid plants with re-blooming characteristics. This new variety, hereinafter referred to as 'HOMLEC', was discovered as a seedling, resulting from the crossing of *Rhododendron* 'Red Slipper', unpatented with the pollen parent *Rhododendron* 'Conleb' U.S. Plant Pat. No. 10,581. The cross was performed during 2000, and the new variety selected by the inventor during 2004 in Independence, La.

After identifying the new variety as a potentially interesting selection, the inventor first organized propagation of 'HOMLEC' by vegetative cuttings during Fall of 2004 at a commercial nursery in Independence, La. The inventor continued confidential and controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'HOMLEC' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'HOMLEC' These characteristics in combination distinguish 'HOMLEC' as a new and distinct *Rhododendron* cultivar:

1. Unique Spring, Summer, and Fall blooming.
2. Red-orange flowers.

3. Easily propagated with semi-hardwood cuttings in late Spring through the Summer.
4. Good specimen plant.
5. Excellent performance in containers.
6. Vigorous growth under normal fertilization and moisture conditions.
7. Upright plant habit.
8. Hardy to Zone 7.
9. Attracts butterflies.
10. Large, single flowers.

COMPARISON TO PARENT VARIETY

'HOMLEC' is similar in most horticultural characteristics to the seed parent variety *Rhododendron* hybrid 'Red Slipper'. Plants of the new cultivar 'HOMLEC' however, produce red-orange flowers compared to the pink flowers of the parent variety. Additionally, plant habit is overall less compact in the new variety, compared to the seed parent.

'HOMLEC' is similar in most horticultural characteristics to the pollen parent *Rhododendron* hybrid 'Conleb'. Plants of the new cultivar 'HOMLEC' however, produce single flowers, whereas 'Conleb' produces deep orange red semi-double flowers. Additionally, plant habit of 'HOMLEC' is narrow and upright whereas the pollen parent has a plant shape which is more globose.

COMMERCIAL COMPARISON

'HOMLEC' can be compared to the commercial variety *Rhododendron* hybrid 'Roblen' U.S. Plant Pat. No. 16,248. Plants of the new cultivar 'HOMLEC' are similar to plants of 'Roblen' in most horticultural characteristics, however, plants of the new cultivar 'HOMLEC' produce single flowers whereas as flowers of 'Roblen' are semi-double. Additionally, flowers of 'HOMLEC' are darker than flowers of 'Roblen'.

BRIEF DESCRIPTION OF THE PHOTOGRAPH

The accompanying photograph in FIG. 1 illustrates in full color a close up of typical flowers of the new variety.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'HOMLEC' plants grown outdoors in Loxley, Ala. Plants are approximately 2 years old, in a 3 gallon nursery container. Measurements and numerical values represent averages of typical plant types.

Botanical classification: *Rhododendron* hybrid 'HOMLEC'.

PROPAGATION

Typically by semi-hardwood cuttings in Spring and Summer.

Root description: Fine, fibrous young roots, well branched. Colored near RHS Grey-Brown 199A.

PLANT

Growth habit: Compact, globular shrub.

Height: Approximately 48 cm to top of foliar and flowering plane.

Plant spread: Approximately 43 cm.

Branching characteristics: Well branched, approximately 4 primary branches from the center of the plant. Branches occur at approximately 45° to 75° angles. Each primary branch has 6 to 10 lateral branches.

Primary branches:

- *Length of primary branches.*—Average 30 cm.
- *Diameter of primary branches.*—Approximately 0.6 cm.
- *Primary branch strength.*—Very strong, difficult to break.
- *Primary branch color.*—Near RHS Yellow-Green 151A, heavily flushed Greyed-Orange 175A. With age, covered with a thin bark like layer colored near Greyed-Orange 174A.
- *Primary branch texture.*—Young growth hirsute. Hairs, approximately 0.15 cm long, colored near Greyed-Orange 175A. Older growth scaly, hirsute. Hairs colored near White 155D.

Lateral branches:

- *Number of lateral branches.*—Approximately 6 to 10 per primary branch.
- *Length of lateral branches.*—Average 12 cm.
- *Diameter of lateral branches.*—Average 0.4 cm.
- *Lateral branch strength.*—Very strong, flexible.
- *Lateral branch color.*—Near RHS Yellow-Green 151A, flushed with Greyed-Orange 175C.
- *Lateral branch texture.*—Hirsute.

Internode length: Average 1.0 cm.

Age of plant described: Approximately 2 years.

FOLIAGE

Leaf:

- *Type.*—Simple.
- *Arrangement.*—Alternate.
- *Average length.*—Approximately 5.0 cm.
- *Average width.*—Approximately 1.9 cm.
- *Shape of blade.*—Broad elliptic.
- *Apex.*—Acute or Murcronate.
- *Base.*—Broad attenuate.
- *Attachment.*—Stalked.
- *Margin.*—Entire.
- *Texture of top surface.*—Pubescent. Hairs appressed.
- *Texture of bottom surface.*—Pubescent. More hairs present along main vein and margin.
- *Color.*—Young foliage upper side: Near RHS Yellow-Green 146A. Young foliage under side: Near RHS Yellow-Green 146C. Mature foliage upper side: Near RHS Green 139A. Mature foliage under side: Near RHS Yellow-Green 146C.
- *Venation.*—Type: Pinnate. Venation color upper side: Near RHS Yellow-Green 153D. Venation color under side: Near RHS Yellow-Green 153B.
- *Petiole.*—Length: About 1.2 cm. Diameter: About 0.3 cm. Color: Upper Surface: Near RHS Yellow-Green 153D. Lower Surface: Near RHS Yellow-Green 153B.

FLOWER

Bloom period: Plants flower in the Spring, then begin intermittent flowering cycles in late Spring/Summer through Fall.

Flower:

- *Arrangement.*—Axillary clusters of perfect, open funnel shaped individual flowers. Typically 5 to 10 flowers per cluster.

Inflorescence:

- *Height.*—Average 10.0 cm.
- *Diameter.*—Average 12.0 cm.

Peduncle:

- *Length.*—Average 4.0 cm.
- *Diameter.*—0.3 cm.
- *Color.*—Near RHS Yellow-Green 151A, slightly flushed with Greyed-Orange 175C.
- *Texture.*—Densely pubescent.
- *Aspect.*—Straight to very slightly curved. Angle of attachment, approximately 35° angle from stem.

Flowers:

- *Length.*—Average 3.9 cm.
- *Diameter.*—Average 6.0 cm.
- *Facing direction.*—Outwardly and upwardly facing.
- *Persistent or self-cleaning.*—Petals self-cleaning.
- *Fragrance.*—None.
- *Tube.*—Tube length: Approximately 1.6 cm. Tube width a widest point: Approximately 1.8 cm. Tube width and narrowest point: Approximately 0.9 cm.
- *Petals.*—Unfused petal segments: Length: Approximately 2.5 cm. Width: Approximately 2.7 cm Apex: Blunt, rounded with shallow, irregular lobes. Shape of petal: Unfused portion, obovate. Petal margin: Entire. Petal Arrangement: Approximately ⅓ fused from base. Petal Number: 5. Petal Texture: Smooth. Color: Upper surface at first opening: Near RHS Orange-Red N34A. Under surface at first opening: Near RHS Orange-Red N34A. Inner surface at maturity: Near RHS Red 42A. Outer surface at maturity: Near RHS Red 42B. Upper surface at fading: Near RHS Red 42B. Under surface at fading: Near RHS Red 42B.

Bud:

- *Shape.*—Elliptic.
- *Length.*—2.9 cm.
- *Diameter.*—1.2 cm.
- *Color.*—Near RHS Orange-Red N34A.

Calyx/sepals:
*Quantity per flower.*—5 sepals.
*Shape*.—Narrow deltate.
*Length.*—0.8 cm.
*Width.*—0.3 cm.
*Apex*.—Acute.
*Base*.—Fused.
*Margin*.—Entire.
*Texture*.—Highly pubescent.
*Color*.—Inner Surface: Near RHS Green 137A. Outer Surface: Near RHS Green 137A.

REPRODUCTIVE ORGANS

Stamens:
*Number.*—10.
*Length.*—3.0 cm.
*Width.*—0.1 cm.
*Color*.—Near RHS Red 42A.
*Anthers*.—Length: Approximately 0.3 cm. Color: Near RHS Red 46B. Pollen: Scant, colored near Greyed-Orange 164D.

Pistil:
*Number.*—1.
*Length.*—4.2 cm.
*Style*.—Length: 3.9 cm. Color: Near RHS Red 42A.
*Stigma*.—Globular, colored near Red 46A.
*Ovary*.—Sericeous texture. Approximately 0.3 cm in diameter. Colored near Red 46B.

OTHER CHARACTERISTICS

Disease and pest resistance: Not observed to be susceptible nor resistant to normal diseases and pests of *Rhododendron* hybrid.
Temperature tolerance: USDA Zone 6.
Fruit/seed production: Not observed to date.

What is claimed is:

1. A new and distinct cultivar of *Rhododendron* plant named 'HOMLEC' as herein illustrated and described.

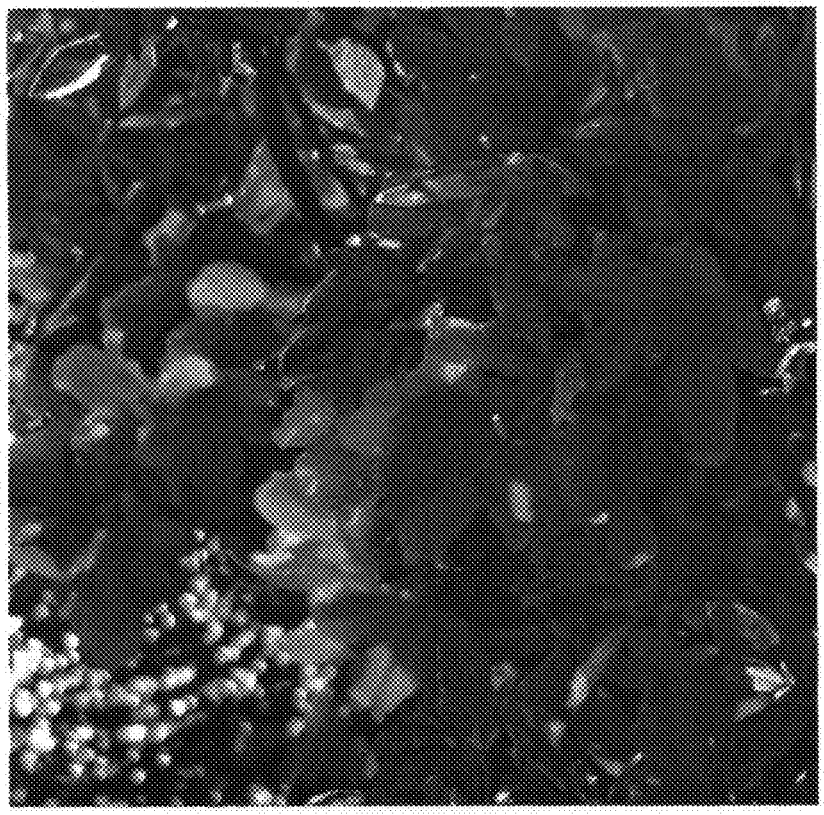

* * * * *